(12) United States Patent
Peal

(10) Patent No.: US 9,145,397 B2
(45) Date of Patent: Sep. 29, 2015

(54) PROCESS FOR THE PREPARATION OF 1-(2-METHYL-4-(2,3,4,5-TETRAHYDRO-1-BENZAZEPIN-1-YLCARBONYL) BENZYLCARBAMOYL)-L-PROLINE-N, N-DIMETHYLAMIDE

(75) Inventor: Valerie Elizabeth Peal, Cardiff (GB)

(73) Assignee: Vantia Limited, Southampton (GB)

( * ) Notice: Subject to any disclaimer, the term of this patent is extended or adjusted under 35 U.S.C. 154(b) by 135 days.

(21) Appl. No.: 14/008,647

(22) PCT Filed: Mar. 30, 2012

(86) PCT No.: PCT/GB2012/050720
§ 371 (c)(1),
(2), (4) Date: Sep. 30, 2013

(87) PCT Pub. No.: WO2012/131389
PCT Pub. Date: Oct. 4, 2012

(65) Prior Publication Data
US 2014/0066619 A1  Mar. 6, 2014

Related U.S. Application Data

(60) Provisional application No. 61/469,904, filed on Mar. 31, 2011.

(30) Foreign Application Priority Data

Mar. 31, 2011 (GB) .................................. 1105537.3

(51) Int. Cl.
*C07D 403/12* (2006.01)
(52) U.S. Cl.
CPC .................................. *C07D 403/12* (2013.01)

(58) Field of Classification Search
CPC ...................................................... C07D 403/12
USPC ............................................................ 540/593
See application file for complete search history.

(56) References Cited

U.S. PATENT DOCUMENTS

2011/0071084 A1   3/2011  Kondo et al.
2014/0296213 A1*  10/2014  Johan et al. .............. 514/217.08

FOREIGN PATENT DOCUMENTS

| WO | WO 01/49682   | 7/2001  |
|----|---------------|---------|
| WO | WO 02/00626   | 1/2002  |
| WO | WO 2011/121308| 10/2011 |
| WO | WO 2012/131389| 10/2012 |

OTHER PUBLICATIONS

Aaltonen et al., "Hyphenated Spectroscopy as a Polymorph Screening Tool", Journal of Pharmaceutical and Biomedical Analysis, 2007, 44, 477-483.
International Patent Application No. PCT/GB2012/050720: International Search Report dated Jul. 20, 2012, 9 pages.
"Screening (Polymorphs Salts Cocrystals)", SSCI Inc., 2009, accessed Jun. 24, 2011, 4 pages.
United Kingdom Patent Application No. GB1105537.3: Search Report dated Jun. 24, 2011, 4 pages.
Yea et al., "New Benzylureas as a Novel Series of Potent, Nonpeptidic Vasopressin V2 Receptor Agonists", J. Med. Chem., Oct. 2008, 51, 8124-8134.

* cited by examiner

Primary Examiner — Brenda Coleman
(74) Attorney, Agent, or Firm — Baker & Hostetler LLP

(57) ABSTRACT

The present invention relates to a new process for the preparation of a crystalline polymorph of a vasopressin $V_2$ agonist.

9 Claims, 4 Drawing Sheets

Figure 2:
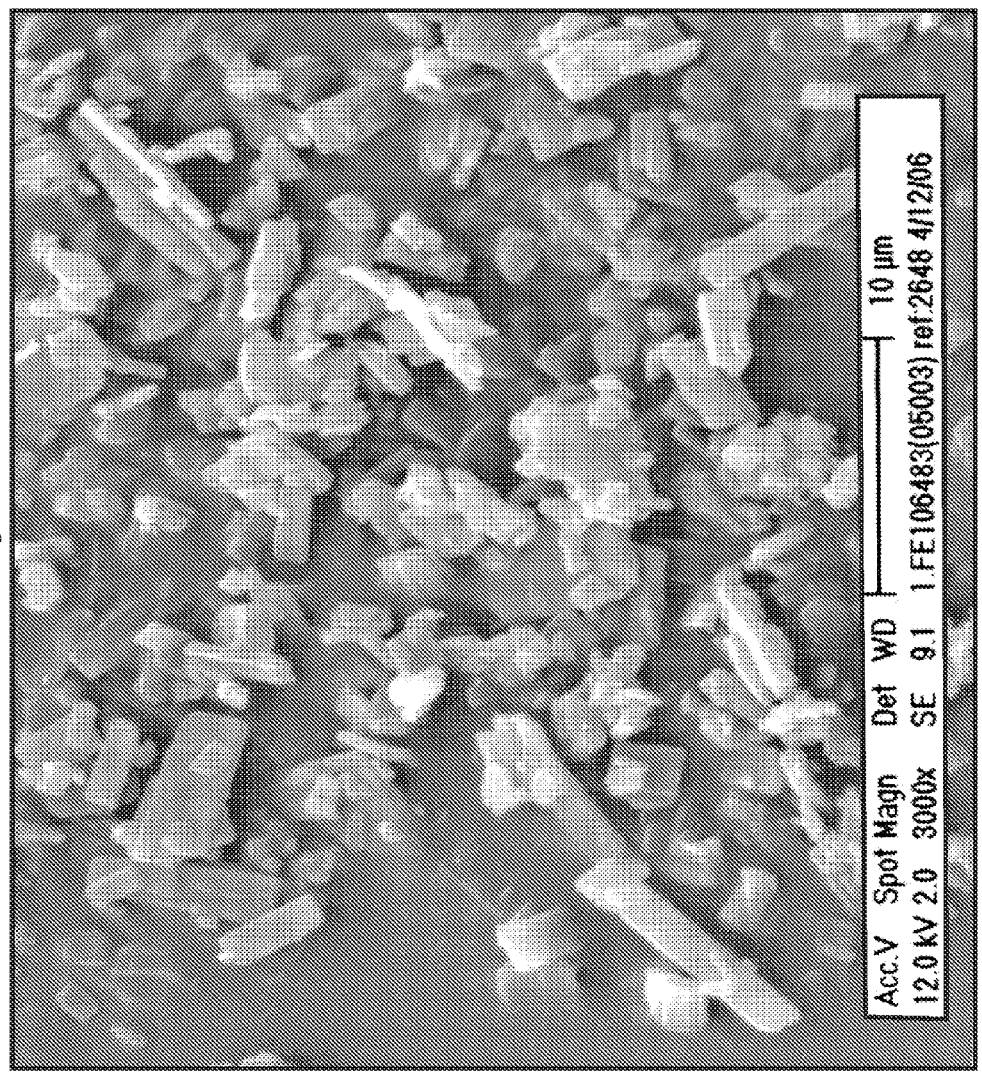

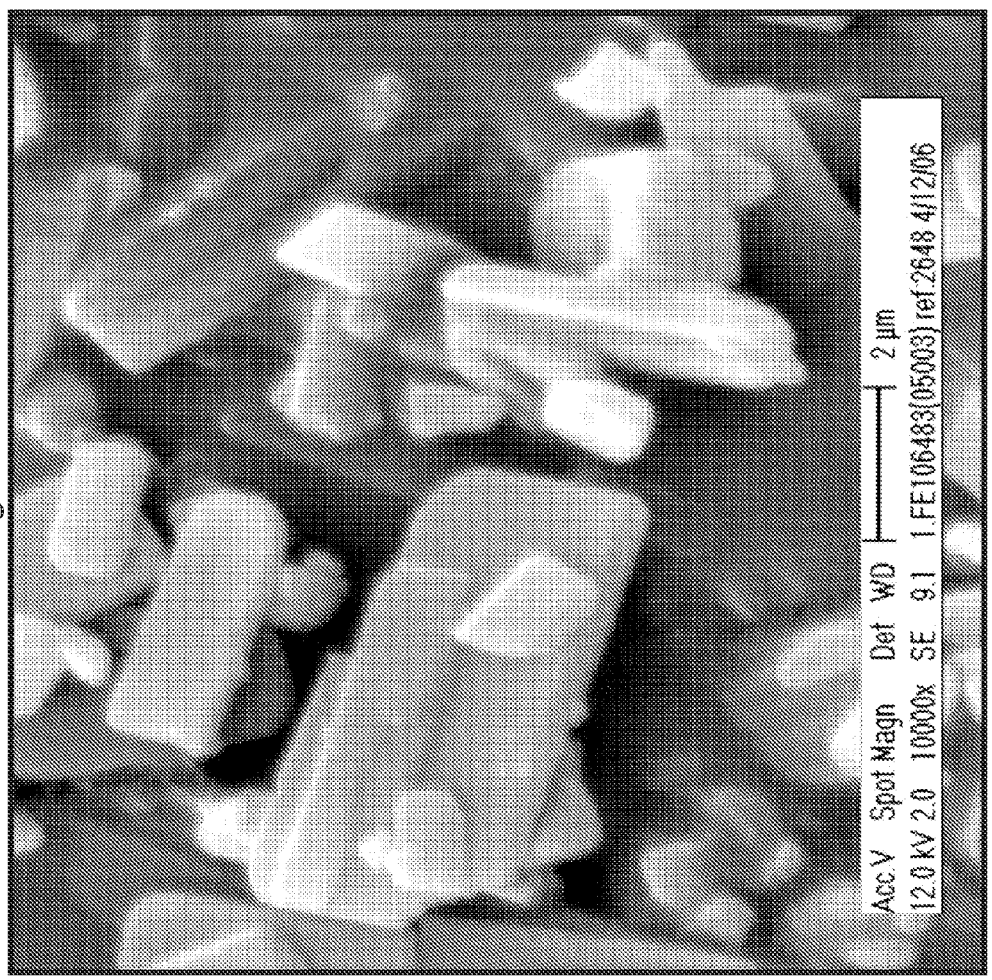
FIG. 2 (contd.)

PROCESS FOR THE PREPARATION OF 1-(2-METHYL-4-(2,3,4,5-TETRAHYDRO-1-BENZAZEPIN-1-YLCARBONYL) BENZYLCARBAMOYL)-L-PROLINE-N, N-DIMETHYLAMIDE

CROSS-REFERENCE TO RELATED APPLICATIONS

This application is the National Stage of International Application No. PCT/GB2012/050720, filed Mar. 30, 2012, which claims the benefit of Great Britain Application No. 1105537.3, filed Mar. 31, 2011, and U.S. Application No. 61/469,904, filed Mar. 31, 2011, the disclosures of which are incorporated herein by reference in their entirety.

The present invention relates to a new process for the preparation of a crystalline polymorph of a vasopressin $V_2$ agonist, 1-(2-methyl-4-(2,3,4,5-tetrahydro-1-benzazepin-1-ylcarbonyl)benzylcarbamoyl)-L-proline-N,N-dimethylamide [CAS 347887-36-9],

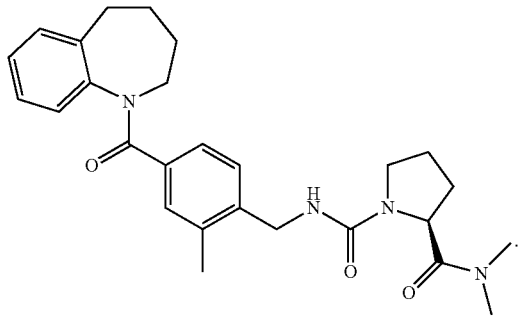 [SMILES: Cc1cc(C(=O)N2CCCCc3ccccc32)ccc1CNC(=O)N1CCC[C@H]1C(=O)N(C)C]

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound. Furthermore, if the active compound is to be incorporated into a dosage form for oral administration, such as a tablet, it is desirable that the active compound be readily micronised to yield a powder with good flow properties to aid manufacture.

With regard to the process for producing the compound, it must be consistent, repeatable and capable of being carried out on an industrial scale. Moreover, the process must be efficient (e.g. require the use of the minimum amount of solvents/reagents and energy) in order that it is economically viable.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley Veil). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

1-(2-methyl-4-(2,3,4,5-tetrahydro-1-benzazepin-1-ylcarbonyl)benzylcarbamoyl)-L-proline-N,N-dimethylamide was first described in international patent application WO 2001/049682 (PCT/GB2001/000023). However, the preparation described in PCT/GB2001/000023 yields an amorphous solid, which was found to be hygroscopic by Gravimetric Vapour Sorption Analysis (GVA). Moreover, scanning electron micrographs (SEM) of this amorphous form show it to consist of irregular, predominantly large (>5 μm in diameter) aggregates. These properties of the amorphous form render it less suitable for use in a manufacturing process.

Various methods described in the known art (WO 2001/049682, WO 2002/000626 and in Yea et al, "New Benzylureas as a Novel Series of Potent, Non-peptidic Vasopressin $V_2$ Receptor Agonists", Journal of Medicinal Chemistry (2008), 51(24), 8124-8134) have been applied to the synthesis of 1-(2-methyl-4-(2,3,4,5-tetrahydro-1-benzazepin-1-ylcarbonyl)benzylcarbamoyl)-L-proline-N,N-dimethylamide by the applicant but all have afforded an amorphous solid (known hereinafter as "the amorphous form"). In light of these investigations, it appeared extremely unlikely that a crystalline form of 1-(2-methyl-4-(2,3,4,5-tetrahydro-1-benzazepin-1-ylcarbonyl)benzylcarbamoyl)-L-proline-N,N-dimethylamide would ever be found.

Unexpectedly, however, it has now been found possible to prepare a stable, crystalline solid form of 1-(2-methyl-4-(2,3,4,5-tetrahydro-1-benzazepin-1-ylcarbonyl)benzylcarbamoyl)-L-proline-N,N-dimethylamide (known hereinafter as "the crystalline form"), which has advantageous physicochemical properties, for example, with regard to chemical stability, hygroscopicity, processability, morphology and technical feasibility. The crystalline form is described by the applicant in a co-pending patent application.

The process first adopted for the preparation of the crystalline form comprised suspending the amorphous form in water and stirring for a prolonged period. When carried out on a modest scale (~15 g of amorphous material), the transformation took 12 days to complete. Thus, if scaled up, the transformation could take much longer, which would have significant economic disadvantages within a manufacturing context.

Accordingly, although the process first adopted for the preparation of the crystalline form provided an adequate route for the production of the crystalline form on a laboratory scale, there was a clear need for a robust process that would be more applicable to the industrial scale manufacture of this compound. To meet this need, the applicant has developed a new and unusual process for the preparation of the crystalline form, which is suitable for use on an industrial scale. Moreover, the process reliably and consistently produces a product that is suitable for formulation as a pharmaceutical.

During the development of the new process, it was found that when 1-(2-methyl-4-(2,3,4,5-tetrahydro-1-benzazepin-1-ylcarbonyl)benzylcarbamoyl)-L-proline-N,N-dimethylamide is dissolved in a solvent system from which it is to be crystallised, for example acetone/water, it displays unexpected and surprising behaviour, which would normally be associated with that of a non-ionic surfactant. Non-ionic surfactant behaviour is typically observed in molecules Which are surrounded by a hydrate shell at lower temperatures which allows for their complete solubility. An increase in temperature causes cleavage of the hydrogen bonds and the compound's solubility is rapidly decreased resulting in the compound separating out from the solution as an oil. Using surfactant terminology, this phase separation and sudden onset of turbidity when the temperature is raised is known as the "cloud point".

Despite the fact that the structure of 1-(2-methyl-4-(2,3,4,5-tetrahydro-1-benzazepin-1-ylcarbonyl)benzylcarbamoyl)-L-proline-N,N-dimethylamide is very different from well known non-ionic surfactants, such as, for example, Triton X-100, a "cloud point" at approximately 38° C. is observed when a solution of 1-(2-methyl-4-(2,3,4,5-tetrahydro-1-benzazepin-1-ylcarbonyl)benzylcarbamoyl)-L-proline-N N-dimethylamide in acetone/water (20/80) is heated. By analogy to surfactant precedent, but without being bound by any particular theory, a hydrate shell surrounding the compound would be anticipated below the cloud point and it is assumed that this increased order of molecular organisation would be an important structural prelude to crystallisation of the hydrate. The loss of the hydrated shell would encourage phase separation and loss of molecular organisation Which would intuitively disfavour formation of the crystalline hydrate. This behaviour is unusual and would not be expected of a compound such as 1-(2-methyl-4-(2,3,4,5-tetrahydro-1-benzazepin-1-ylcarbonyl)benzyl carbamoyl)-L-proline-N N-dimethylamide. The typical behaviour of non-ionic surfactants is described in publications such as M. Alauddin, T. Parvin & T. Begum, *Journal of Applied Sciences*, (2009), 9, 2301-2306; P. Huibers, D. Shah & A. Katritzky, *Journal of Colloid and Interface Science*, (1997), 193, 132-136; T. Inoue, H. Ohmura & Murata, *Journal of Colloid and Interface Science*, (2003), 258, 374-382; T. Iwanaga & H. Kunieday, *Journal of Colloid and Interface Science*, (2000), 227, 349-355; H. Schott, *Colloids and Surfaces* A, (2001), 186, 129-136; and D. Myers, 2005, Surfactant Science and Technology, 3$^{rd}$ Edition, Oxford University Press, New York, ISBN:978-0-471-68024-6.

In accordance with the present invention, there is provided a process for the preparation of a crystalline polymorph of 1-(2-methyl-4-(2,3,4,5-tetrahydro-1-benzazepin-1-ylcarbonyl)benzylcarbamoyl)-L-proline-N,N-dimethylamide comprising the steps of;
i) adding 1-(2-methyl-4-(2,3,4,5-tetrahydro-1-benzazepin-1-ylcarbonyl)benzylcarbamoyl)-L-proline-N,N-dimethylamide to an organic solvent;
ii) heating the mixture until an emulsion is formed;
iii) cooling the emulsion until a clear solution is obtained;
iv) stirring the clear solution until a suspension is obtained; and
v) isolating the resulting crystalline form of 1-(2-methyl-4-(2,3,4,5-tetrahydro-1-benzazepin-1-ylcarbonyl)benzylcarbamoyl)-L-proline-N,N-dimethylamide.

Suitable organic solvents include ethyl acetate, heptane tetrahydrofuran, iso-butyl acetate, n-butyl acetate, ethanol, isoamyl alcohol, 2-methyltetrahydrofuran, methyl iso-butyl ketone, 2-hexanone, 2-pentanone, acetone, n-propyl acetate, methyl ethyl ketone, and iso-propanol.

Preferably, the process of the present invention is carried out in an organic solvent in the presence of water. Within the context of the present invention, the term "aqueous organic solvent" is used to described solvent systems where water is added to the organic solvent, water is present in the organic solvent as supplied (i.e. a non-anhydrous solvent), or water is present in the starting material (i.e. 1-(2-methyl-4-(2,3,4,5-tetrahydro-1-benzazepin-1-ylcarbonyl)benzylcarbamoyl)-L-proline-N,N-dimethylamide).

Suitable aqueous organic solvents include mixtures of ethyl acetate, heptane and water; tetrahydrofuran and water; iso-butyl acetate and water; n-butyl acetate and water; ethanol and water; isoamyl alcohol and water; 2-methyltetrahydrofuran and water; methyl iso-butyl ketone and water; 2-hexanone and water; 2-pentanone and water; acetone and water; n-propyl acetate and water; methyl ethyl ketone and water; and iso-propanol and water. n-Heptane may optionally be added to the mixture of an organic solvent and water.

In an aspect of the invention, the aqueous organic solvent is selected from acetone and water; n-propyl acetate and water; methyl ethyl ketone and water; and iso-propanol and water. n-Heptane may optionally be added to the mixture of an organic solvent and water.

In an aspect of the invention, the aqueous organic solvent is a mixture of acetone and water. n-Heptane may optionally be added to this mixture.

In an aspect of the invention, the aqueous organic solvent is acetone/water (20:80). n-Heptane may optionally be added to this mixture.

According to an aspect of the invention, in process step ii), the mixture of 1-(2-methyl-4-(2,3,4,5-tetrahydro-1-benzazepin-1-ylcarbonyl)benzylcarbamoyl)-L-proline-N,N-dimethylamide the aqueous organic solvent is heated to a temperature of approximately 40-60° C. In an aspect of the invention, the mixture is heated to a temperature of approximately 45-55° C. In an aspect of the invention, the mixture is heated to a temperature of approximately 60° C. in an aspect of the invention, the mixture is heated to a temperature of approximately 55° C. In an aspect of the invention, the mixture is heated to a temperature of approximately 50° C. In an aspect of the invention, the mixture is heated to a temperature of approximately 45° C. In an aspect of the invention, the mixture is heated to a temperature of approximately 40° C.

According to an aspect of the invention, in process step iii), the emulsion is cooled to a temperature of approximately 20-35° C. In an aspect of the invention, the emulsion is cooled to a temperature of approximately 24-30° C. In an aspect of the invention, the emulsion is cooled to a temperature of approximately 34° C. In an aspect of the invention, the emulsion is cooled to a temperature of approximately 32° C. In an aspect of the invention, the emulsion is cooled to a temperature of approximately 30° C. In an aspect of the invention, the emulsion is cooled to a temperature of approximately 28° C. In an aspect of the invention, the emulsion is cooled to a temperature of approximately 26° C. In an aspect of the invention, the emulsion is cooled to a temperature of approximately 25° C. In an aspect of the invention, the emulsion is cooled to a temperature of approximately 24° C.

According to an aspect of the invention, the process further comprises the addition of crystalline seeds of 1-(2-methyl-4-(2,3,4,5-tetrahydro-1-benzazepin-1-ylcarbonyl)benzylcarbamoyl)-L-proline-N,N-dimethylamide following process step iii).

According to an aspect of the invention, in process step iv), the clear solution is stirred for a period of 10-100 hours. In an aspect of the invention, the clear solution is stirred for a period of 20-90 hours. In an aspect of the invention, the clear solution is stirred for a period of 30-90 hours. In an aspect of the invention, the clear solution is stirred for a period of 40-90 hours. In an aspect of the invention, the clear solution is stirred for a period of 50-90 hours.

According to an aspect of the invention, in process step v), the crystalline form is isolated by filtration.

According to an aspect of the invention, following process step v), the crystalline form is dried. In an aspect of the invention, the crystalline form is air dried. In an aspect of the invention, the crystalline form is dried in vacuo.

In an aspect, the present invention provides a crystalline form of the invention when manufactured by a process according to the invention.

The crystalline form of the present invention has a number of therapeutic applications, particularly in the treatment of diseases or conditions mediated by vasopressin $V_2$. Such diseases or conditions include nocturnal enuresis, nocturia, polyuria resulting from central diabetes insipidus, urinary incontinence and bleeding disorders.

Figure 1:
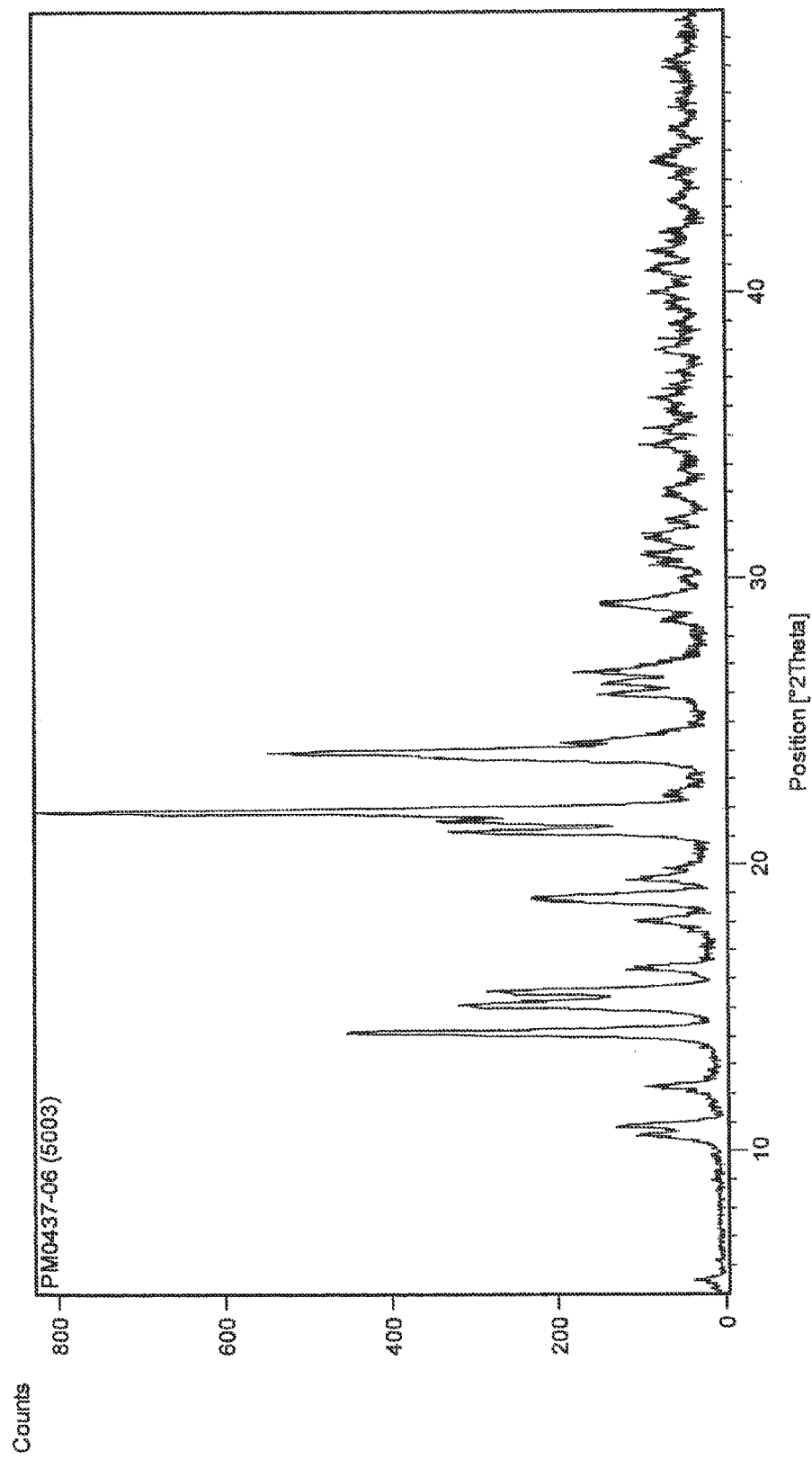

The invention will now be illustrated by the following non-limiting examples. In the examples the following figures are presented:

FIG. 1: X-ray powder diffraction pattern of a crystalline form of 1-(2-methyl-4-(2,3,4,5-tetrahydro-1-benzazepin-1-ylcarbonyl)benzylcarbamoyl)-L-proline-N,N-dimethylamide.

FIG. 2: SEM images of a crystalline form of 1-(2-Methyl-4-(2,3,4,5-tetrahydro-1-benzazepin-1-ylcarbonyl)benzylcarbamoyl)-L-proline-N,N-dimethylamide.

Figure 3:
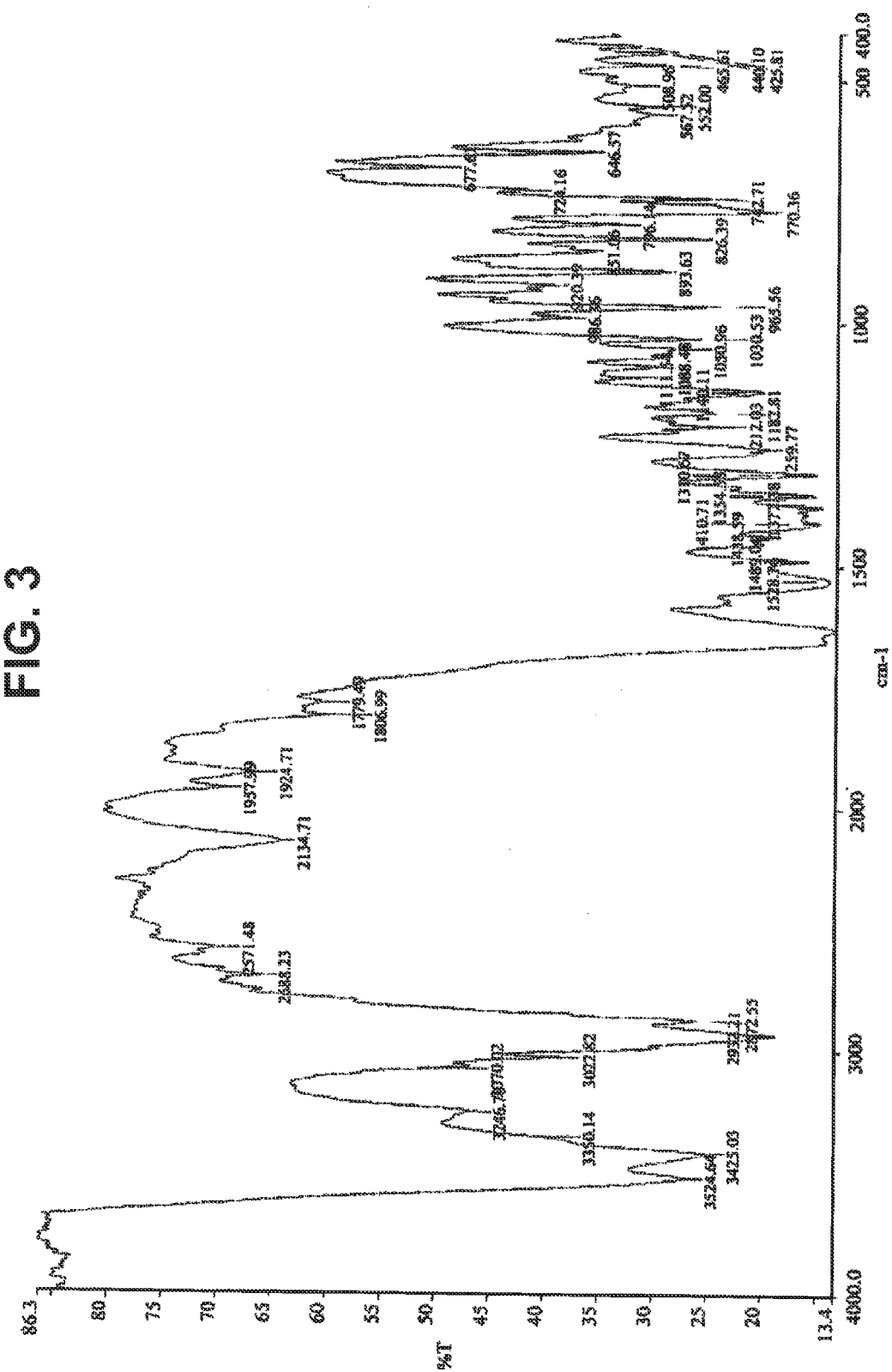

FIG. 3: IR spectrum of a crystalline form of 1-(2-methyl-4-(2,3,4,5-tetrahydro-1-benzazepin-1-ylcarbonyl)benzylcarbamoyl)-L-proline-N,N-dimethylamide.

General Experimental Details

All solvents and commercial reagents were used as received.

Differential scanning calorimetry (DSC):

Approximately 1 to 3 mg of the sample was accurately weighed into an aluminium DSC pan and sealed using a non-hermetic lid. Subsequently, the sample was loaded into a Mettler 12E DSC Instrument equipped with a Julabo F25 cooling unit. The samples were heated from 50 to 200° C. at 10° C./min and the change in heat-flow response monitored. The instrument had been previously calibrated using a twin point calibration of indium and lead reference standards as required.

Hyper differential scanning calorimetry: Approximately 1 to 3 mg of the sample was accurately weighed into an aluminium DSC pan and sealed using a non-hermetic lid. Subsequently, the sample was loaded into a Diamond DSC (Perkin-Elmer Instruments, US) equipped with a liquid nitrogen cooling unit and cooled to 0° C. Once a stable baseline had been attained, the samples were heated from 0 to 200° C. at 200° C./min and the change in heat-flow response monitored. A helium purge gas was used at a flow rate of 20 ml/min in order to improve the heat transfer process from the sample to the thermocouples and ultimately improve sensitivity. Prior to analysis the instrument was temperature and heat-flow calibrated using an indium reference standard.

Infra-red spectra were measured using a system set to a Diffuse Reflectance configuration, with samples prepared with potassium bromide, and scanned from 4000 $cm^{-1}$ to 400 $cm^{-1}$.

X-Ray Powder Diffraction (XRPD) patterns were collected using sample weights of approximately 2-10 mg, which was gently compressed on the XRPD zero background single obliquely cut silica sample holder. The sample was then loaded into a Philips X-Pert MPD diffractometer and analysed using the following experimental conditions:

Tube anode: Cu
Generator tension: 40 kV
Tube current: 40 mA
Wavelength alpha1: 1.5406 Å
Wavelength alpha2: 1.5444 Å
Start angle [2 θ]: 5
End angle [2 θ]: 50
Time per step: 2.5 seconds (X-Pert MPD) or 31 seconds (X-Pert Pro).

Scanning electron micrographs were produced by coating the desired material with a thin layer of gold (sputter coating) and examined using a FEE-Philips XL30 Scanning S electron microscope. The acceleration voltage of the electrons used for analysis was 10 KV. All images were captured with a computer controlled CCD camera attachment.

1-(2-methyl-4-(2,3,4,5-tetrahydro-1-benzazepin-1-ylcarbonyl)benzylcarbamoyl)-L-proline-N,N-dimethylamide (Crystalline Form)

Method A (Comparative Example)

1-(2-Methyl-4-(2,3,4,5-tetrahydro-1-benzazepin-1-ylcarbonyl)benzylcarbamoyl)-L-proline-N,N-dimethylamide (15.0 g; prepared using the method described in PCT/GB2001/000023) was suspended in water (1000 mL) and stirred for 12 days. The mixture was filtered and the solid washed with ice-cold water. The solid was dried at 60° C. to constant weight to afford the crystalline solid form as a white powder.

Method B 1-(2-Methyl-4-(2,3,4,5-tetrahydro-1-benzazepin-1-ylcarbonyl)benzylcarbamoyl)-L-proline-N,N-dimethylamide (300 mg; prepared using the method described in PCT/GB2001/000023) was suspended in acetone/water 20/80 (1 mL) and heated to 50° C. to give an emulsion. The mixture was cooled to 30° C. and stirred to give an opaque solution at 30° C. The temperature was reduced to 28° C. to give a clear solution. Stirring was continued for 18 hours to give a suspension and stirred for an additional 30 hours. The solids were removed by filtration, washed with acetone/water 20/80, air dried for 10 minutes and dried further in dessicator for 1 hour to afford the crystalline solid form as a white powder (76% yield).

Method C 1-(2-Methyl-4-(2,3,4,5-tetrahydro-1-benzazepin-1-ylcarbonyl)benzylcarbamoyl)-L-proline-N,N-dimethylamide (200 g; prepared using the method described in PCT/GB2001/000023) was added to a mixture of acetone/water (20/80) (500 mL) and stirred at 15° C. for 5 minutes. The mixture was heated to 50° C. over 15 minutes to give an emulsion, stirred at 50° C. for 10 minutes and cooled to 27° C. over 38 minutes to give a clear solution. A "cloud point" was noted at approximately 38° C. during cooling. Seeds of the crystalline 1-(2-methyl-4-(2,3,4,5-tetrahydro-1-benzazepin-1-ylcarbonyl)benzylcarbamoyl)-L-proline-N,N-dimethylamide (Form 1) (10 g) were suspended in a mixture of acetone/water (20/80) (25 mL) and added to the reaction mixture. A further amount of acetone/water (20/80) (25 mL) was used to rinse residual seed suspension into the mixture. The suspension was left to stir at 27° C. until the total experiment time reached 46 hours. The suspension was cooled to 20° C. over 1 hour and was stirred for a further 42 hours at 20° C. The suspension was filtered and the solids air dried for approximately 30 minutes. The solids were washed with mixtures of acetone/water (5/95, 3×100 mL) and air dried for approximately 3 hours. The solids were dried further at 45° C. in vacuo to afford the crystalline solid form as a white powder, yield 166 g (76%).

An XRPD diffractogram of 1-(2-methyl-4-(2,3,4,5-tetrahydro-1-benzazepin-1-ylcarbonyl)benzylcarbamoyl)-L-proline-N,N-dimethylamide (Crystalline Form) is shown in FIG. 1.

Peak Position Table:

| Pos. [°2Th.] | Height [cts] | FWHM [°2Th.] | d-spacing [Å] | Rel. Int. [%] |
|---|---|---|---|---|
| 5.4754 | 52.82 | 0.1968 | 16.14063 | 3.95 |
| 10.5691 | 141.1 | 0.1574 | 8.37046 | 8.44 |
| 10.9029 | 156.56 | 0.1968 | 8.11496 | 11.71 |
| 12.2633 | 74.39 | 0.2755 | 7.2176 | 7.79 |
| 14.1671 | 526.77 | 0.2362 | 6.2517 | 47.29 |
| 15.1107 | 354.54 | 0.2755 | 5.86334 | 37.13 |
| 15.5663 | 308.05 | 0.2165 | 5.69277 | 25.35 |
| 16.3567 | 118.47 | 0.2755 | 5.4194 | 12.41 |
| 18.0376 | 92.63 | 0.2952 | 4.91799 | 10.39 |
| 18.8113 | 257.21 | 0.433 | 4.71742 | 42.33 |
| 19.517 | 101.18 | 0.2165 | 4.54841 | 8.33 |
| 21.1847 | 351.17 | 0.2362 | 4.19398 | 31.53 |
| 21.5641 | 492.65 | 0.4239 | 4.12103 | 53.65 |
| 21.8694 | 954.78 | 0.2755 | 4.0642 | 100 |
| 23.96 | 600.03 | 0.2558 | 3.7141 | 58.36 |
| 25.9754 | 134.06 | 0.2165 | 3.43033 | 11.03 |
| 26.3607 | 153.56 | 0.1771 | 3.38105 | 10.34 |
| 26.7483 | 157.84 | 0.1968 | 3.33293 | 11.81 |
| 28.5823 | 88.09 | 0.087 | 3.12311 | 1.97 |
| 29.1687 | 142.58 | 0.2755 | 3.06165 | 14.93 |
| 30.5138 | 91.15 | 0.1246 | 2.92967 | 2.92 |
| 30.8276 | 105.54 | 0.1671 | 2.90057 | 4.53 |
| 31.4796 | 66.87 | 0.433 | 2.84196 | 11.01 |
| 32.0522 | 52.67 | 0.2362 | 2.79249 | 4.73 |
| 33.0593 | 49.71 | 0.4723 | 2.70968 | 8.93 |
| 34.6631 | 51.37 | 0.2362 | 2.5879 | 4.61 |
| 35.2115 | 50.8 | 0.2362 | 2.54884 | 4.56 |
| 35.91 | 34.89 | 0.09 | 2.50085 | 0.81 |
| 36.3592 | 67.12 | 0.0542 | 2.47098 | 0.93 |
| 38.0113 | 53.83 | 0.2755 | 2.3673 | 5.64 |
| 39.6353 | 63.12 | 0.087 | 2.27397 | 1.41 |
| 40.0448 | 79.61 | 0.0949 | 2.25165 | 2.91 |
| 40.8189 | 50.25 | 0.2362 | 2.21072 | 4.51 |
| 41.4384 | 50.14 | 0.2362 | 2.17909 | 4.5 |
| 44.6841 | 29.53 | 0.4723 | 2.02806 | 5.3 |
| 48.0156 | 26.93 | 0.576 | 1.89327 | 7.97 |

SEM Analysis:

The SEM images showed that the crystals of 1-(2-methyl-4-(2,3,4,5-tetrahydro-1-benzazepin-1-ylcarbonyl)benzylcarbamoyl)-L-proline-N,N-dimethylamide have rectangular morphology (see FIG. 2).

Infra-red spectroscopy, spectrum comprises peaks at wavelengths of approximately 3525, 3425, 2932, 2873, 2135, 1958, 1925, 1631, 1529, 1489, 1439, 1377, 1355, 1311, 1260, 770, 743 cm$^{-1}$. The spectrum is presented in FIG. 3.

DSC: onset approximately 109.9° C.
Hyper DSC: onset approximately 114° C.

Biological Activity

The ability of the crystalline form of the invention to agonise the vasopressin $V_2$ receptor may be determined using the in vivo assay described in PCT/GB2001/000023.

When tested in this assay, 1-(2-Methyl-4-(2,3,4,5-tetrahydro-1-benzazepin-1-ylcarbonyl)benzylcarbamoyl)-L-proline-N,N-dimethylamide showed 82% inhibition of urine output (at 1 hour) when dosed at 1 mg/Kg.

The invention claimed is:

1. A process for the preparation of 1-(2-methyl-4-(2,3,4,5-tetrahydro-1-benzazepin-1-ylcarbonyl)benzylcarbamoyl)-L-proline-N,N-dimethylamide, comprising the steps of:
   i) adding 1-(2-methyl-4-(2,3,4,5-tetrahydro-1-benzazepin-1-ylcarbonyl)-benzylcarbamoyl)-L-proline-N,N-dimethylamide to an organic solvent;
   ii) heating the mixture until an emulsion is formed;
   iii) cooling the emulsion until a clear solution is obtained;
   iv) stirring the clear solution until a suspension is obtained; and
   v) isolating the resulting crystalline form of 1-(2-methyl-4-(2,3,4,5-tetrahydro-1-benzazepin-1-ylcarbonyl)benzylcarbamoyl)-L-proline-N, N-dimethylamide.

2. The process according to claim 1 wherein the organic solvent is an aqueous organic solvent.

3. The process according to claim 2 wherein the aqueous organic solvent is selected from a mixture of acetone and water; n-propyl acetate and water; methyl ethyl ketone and water; and iso-propanol and water.

4. The process according to claim 1, wherein, in process step ii), the mixture is heated to a temperature of approximately 40-60° C.

5. The process according to claim 1, wherein, in process step iii), the emulsion is cooled to a temperature of approximately 20-35° C.

6. The process according to claim 1, wherein, in process step iv), the clear solution is stirred for a period of 20-90 hours.

7. The process according to claim 1, wherein the process further comprises the addition of crystalline seeds of 1-(2-methyl-4-(2,3,4,5-tetrahydro-1-benzazepin-1-ylcarbonyl)benzylcarbamoyl)-L-proline-N; N-dimethylamide following process step iii).

8. The process according to claim 1, wherein in process step v), the crystalline form is isolated by filtration.

9. The process according to claim 1, wherein the crystalline form is air dried following isolation according to process step v).

* * * * *